United States Patent
Coquerel et al.

(10) Patent No.: US 8,907,106 B2
(45) Date of Patent: Dec. 9, 2014

(54) PROCESS FOR THE RESOLUTION OF ENANTIOMERS BY PREFERENTIAL EVAPORATIVE CRYSTALLIZATION

(75) Inventors: Gerard Coquerel, Mont Saint Aignan (FR); Guillaume Levilain, Deville les Rouen (FR)

(73) Assignee: Universite de Rouen, Mont-Saint-Aignan (FR)

( * ) Notice: Subject to any disclaimer, the term of this patent is extended or adjusted under 35 U.S.C. 154(b) by 380 days.

(21) Appl. No.: 13/516,861

(22) PCT Filed: Dec. 16, 2010

(86) PCT No.: PCT/EP2010/069860
§ 371 (c)(1),
(2), (4) Date: Jun. 18, 2012

(87) PCT Pub. No.: WO2011/073300
PCT Pub. Date: Jun. 23, 2011

(65) Prior Publication Data
US 2012/0259127 A1    Oct. 11, 2012

Related U.S. Application Data

(60) Provisional application No. 61/288,556, filed on Dec. 21, 2009.

(30) Foreign Application Priority Data

Dec. 18, 2009    (FR) ...................................... 09 59170

(51) Int. Cl.
C07D 233/72    (2006.01)
C07B 57/00    (2006.01)

(52) U.S. Cl.
CPC ...................................... *C07B 57/00* (2013.01)
USPC ........................................ 548/317.1; 560/355

(58) Field of Classification Search
CPC ........................................................ C07D 233/72
USPC ........................................ 548/317.1; 560/355
See application file for complete search history.

(56) References Cited

U.S. PATENT DOCUMENTS 6,022,409 A * 2/2000 Coquerel et al. ................. 117/68
2009/0124811 A1 5/2009 Coquerel et al.

FOREIGN PATENT DOCUMENTS

FR    2 920 428 A1    3/2009

OTHER PUBLICATIONS

Arnaud Galland et al.: "Spotting Conglomerates by Second Harmonic Generation", Crystal Growth and Design, vol. 9, No. 6, May 14, 2009, pp. 2713-2718, XP002595590, p. 2713, left-hand column, line 12-line 15.
International Search Report, dated in Feb. 11, 2011, from corresponding PCT application.

* cited by examiner

*Primary Examiner* — Kamal Saeed
*Assistant Examiner* — Janet L Coppins
(74) *Attorney, Agent, or Firm* — Young & Thompson

(57) ABSTRACT

A process for the resolution of two enantiomers which involves inducing the preferential crystallization of one enantiomer by adjusting the composition of a suspension or solution including a racemic mixture of the two enantiomers and a solvent, by evaporation of the latter.

12 Claims, 6 Drawing Sheets

Figure 1:
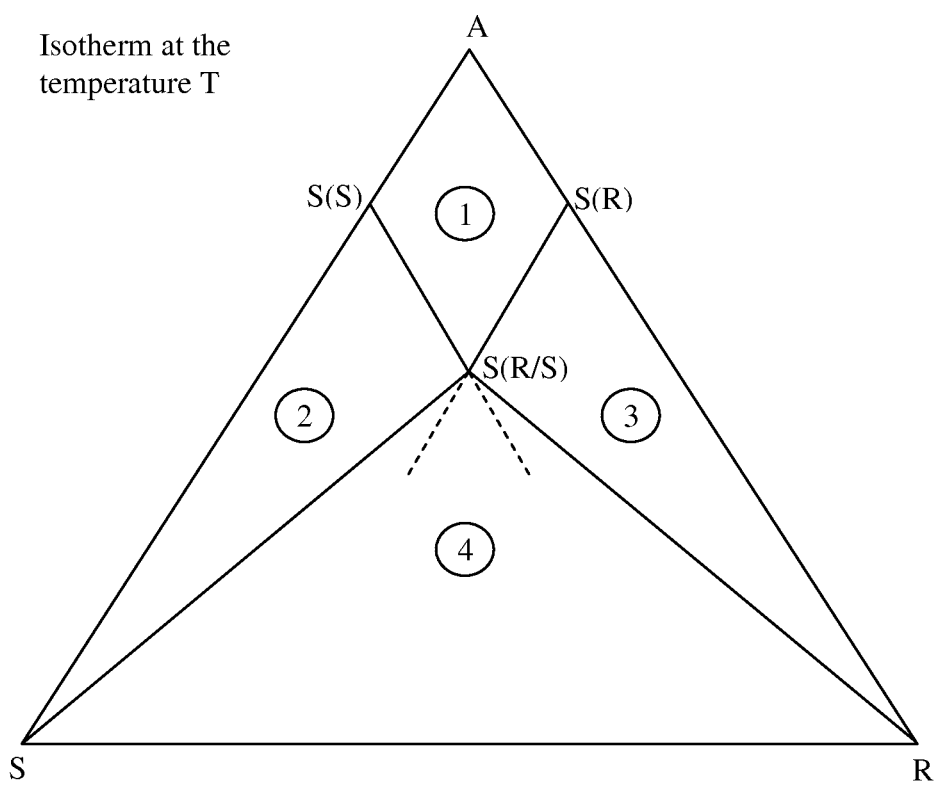

PROCESS FOR THE RESOLUTION OF ENANTIOMERS BY PREFERENTIAL EVAPORATIVE CRYSTALLIZATION

The present invention relates to the field of the separation of two enantiomers (optical antipodes) of a chemical entity by preferential crystallization.

Various techniques are known for separating two optically active compounds. The commonest method consists in reacting a racemic compound with an optically active substance in order to obtain diastereoisomers capable of subsequently being separated by crystallization or chromatography, for example. Other methods for the resolution of enantiomers comprise kinetic separation, which uses the difference in reaction rate of each enantiomer with a chiral reactant, and, similarly, catalytic separation, which makes use of a chiral catalyst, such as an enzyme.

Yet another route for separating two enantiomers is the preferential crystallization technique, which is widely employed in laboratories and in industry by virtue of the advantages which it introduces. Mainly:

it avoids the use of an expensive intermediate chiral agent, the subsequent recovery of which involves losses rarely of less than 10%, the 2 antipodes are obtained directly, in contrast to the method employing conventional resolution by formation of diastereoisomeric salts, the yield is theoretically quantitative as a result of successive recyclings; furthermore, if the product can be racemized (by an additional stage), the yield is then 100% for the desired enantiomer, the purification of the crude enantiomer crystals is easy.

Thus, there has already been described, in the document U.S. Pat. No. 6,022,409, a preferential crystallization process comprising: (a) the preparation of a mixture of crystals in the conglomerate form, of a first enantiomer and of a solvent, (b) the cooling of the mixture according to certain temperature kinetics and under increasing stirring, to promote the growth of said enantiomer while avoiding nucleation of the other enantiomer, and (c) the recovery of the crystals of the first enantiomer. The conglomerate is subsequently added, in a weight equal to the crop, to the mother liquors, in order to obtain a two-phase mixture, from which the second enantiomer is crystallized in its turn by cooling. This process, known as AS3PC (auto-seeded programmed polythermic preferential crystallization), was applied in particular to the resolution of salts of omeprazole in application FR 2 920 428.

Although the processes of the prior art have been successfully applied to the resolution of some enantiomers, the fact nonetheless remains that it would be desirable to have available a constant-temperature preferential crystallization process.

This is because such a process would make it possible:

to resolve heat-sensitive molecules (which decompose chemically following successive heating and cooling operations)

to isolate an enantiomer having a solubility which does not vary in substantial proportions with the temperature (low dS/dT) within easily accessible ranges, such as, for example, the case of sodium 2-chloromandelate in the vicinity of ambient temperature, since supersaturation would be created using a means other than the application of a temperature change (or gradient).

The Inventors have developed a process which makes it possible to meet the above requirements, insofar as it does not require temperature modification. According to this process, the preferential crystallization of an enantiomer is obtained by evaporation of solvent. This is because it has been demonstrated that it is possible to promote the crystallization of one enantiomer by adjusting the composition of the mixture of the two enantiomers with the solvent by evaporation of the latter. Surprisingly, the interfaces created by the gas bubbles generated by this evaporation do not affect the stereoselectivity of the process. In addition, the turbulence brought about by this evaporation and the associated risk of attrition of the crystals do not bring about crystallization of the undesired enantiomer (by heterogeneous germination).

This process furthermore offers a substantial advantage with respect to the processes of the prior art in the case where the solvent is volatile. This is because the preferential crystallization is then much faster, while retaining comparable results to the prior methods, with regard to the weight of solids harvested, the final enantiomeric excess of the mother liquor and the weight of pure enantiomer per cycle, which is reflected by an increased productive output for a given pair of enantiomers, at an identical scale.

A specific subject matter of the present invention is a process for the resolution of two enantiomers by auto-seeded preferential evaporative crystallization, which comprises the stages consisting in:

1) Preparing a suspension comprising a racemic mixture of enantiomers, an excess of the first of the enantiomers and at least one solvent, at a temperature T, so that the overall synthetic mixture $E_i$ representing the composition of the suspension, on the isothermal section at T of the ternary diagram between the pair of enantiomers and the solvent, is located in the two-phase region of the enantiomer in excess, in equilibrium with its saturated solution;

2) Evaporating a portion of the solvent present in the suspension prepared in 1) until a overall synthetic mixture $E_f$ is reached located in the three-phase region of said ternary diagram;

3) Harvesting the crystals of the first enantiomer by filtration;

4) Adding, to the mother liquor resulting from the preceding filtration, the racemic mixture in the form of crystals, and also solvent, so that the overall composition of the system is represented by the point $E'_i$ symmetrical to the point $E_i$, with respect to the plane of the racemic mixture of the system on said isothermal section;

5) Leaving the suspension stirring at the temperature T until the thermodynamic equilibrium is reached;

6) Evaporating substantially the same amount of solvent as during stage 2), so that the overall synthetic mixture reaches a point $E'_f$ located in the three-phase region of said ternary diagram;

7) Harvesting the crystals of the second enantiomer by filtration;

8) Adding, to the mother liquor resulting from the preceding filtration, the racemic mixture in the form of crystals, and also solvent, so that the overall composition of the system is represented by the point $E_i$ on said isothermal section;

9) Leaving the suspension stirring at the temperature T until the thermodynamic equilibrium is reached;

10) Repeating stages 2) to 9) in order to successively obtain one and then the other of the enantiomers.

Another subject matter of the present invention is a process for the resolution of two enantiomers by seeded preferential evaporative crystallization, which comprises the stages consisting in:

1) Preparing a homogeneous solution comprising a racemic mixture of the enantiomers, an excess of the first of the enantiomers and at least one solvent, at a temperature T, so that the point $E_i$ representing the composition of the solution, on the isothermal section at T of the ternary diagram between the pair of enantiomers and the solvent, is located in the single-phase region;

2) Evaporating a portion of the solvent present in the solution prepared in 1), in order to obtain a supersaturated solution;

3) Seeding the solution with the enantiomer in excess;

4) Again evaporating a portion of the solvent, so that the overall synthetic mixture reaches a point $E_f$ located in the three-phase region of said ternary diagram;

5) Harvesting the crystals of the first enantiomer by filtration;

6) Adding, to the mother liquor resulting from the preceding filtration, the racemic mixture in the form of crystals, and also solvent, so that the overall composition of the system is represented by the point $E'_i$ symmetrical to the point $E_i$, with respect to the plane of the racemic mixture of the system on said isothermal section;

7) Leaving the solution stirring at the temperature T until dissolution is complete;

8) Evaporating substantially the same amount of solvent as during stage 2);

9) Seeding the solution with the second enantiomer in excess;

10) Evaporating substantially the same amount of solvent as during stage 4), so that the overall synthetic mixture reaches a point $E'_f$ located in the three-phase region of said ternary diagram;

11) Harvesting the crystals of the second enantiomer by filtration;

12) Adding, to the mother liquor resulting from the preceding filtration, the racemic mixture in the form of crystals, and also solvent, so that the overall composition in the system is represented by the point $E_i$ on said isothermal section;

13) Leaving the solution stirring at the temperature T until the thermodynamic equilibrium is reached;

14) Repeating stages 2) to 13) in order to successively obtain one and then the other of the enantiomers.

The process according to the present invention makes possible the resolution of any pair of chiral compounds (denoted R and S), the racemic mixture of which crystallizes in the form of a stable conglomerate in at least one solvent at, at least, one working temperature T. This expression is understood to mean that, at the temperature T, any mixture in thermodynamic equilibrium of the two enantiomers where the solvent is composed of two types of crystals immiscible in the solid state (or having a limited region of miscibility in the solid state), each containing only molecules of the same configuration (or homochiral molecules) and incorporating or not incorporating solvent molecules (solvates).

According to one embodiment, the process according to the invention can be applied, for example, to the resolution of the enantiomers of sodium 2-chloromandelate or of 5-methyl-5-phenylhydantoin.

Figure 2A:
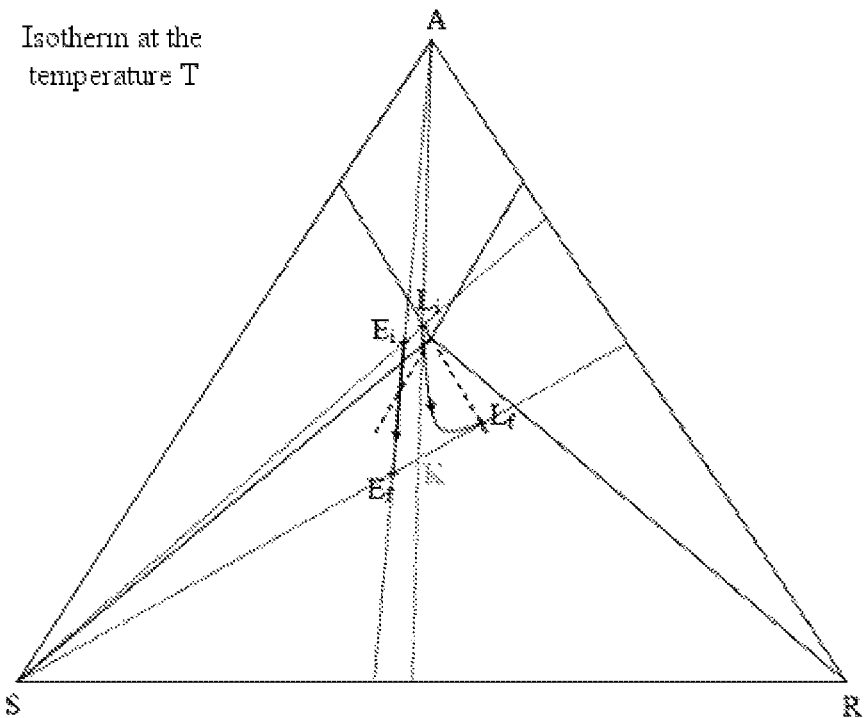
Figure 2B:
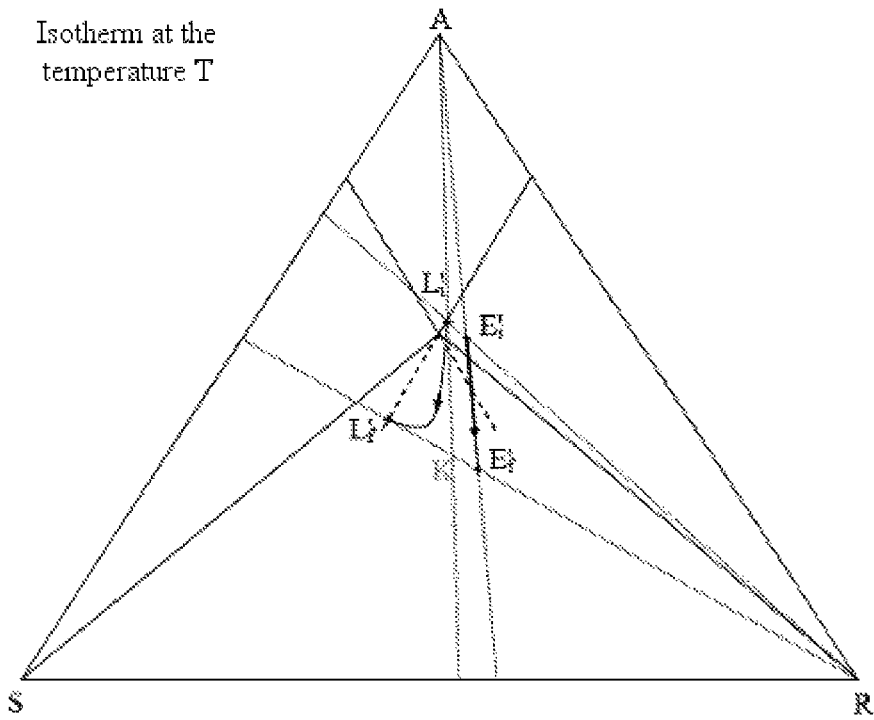
Figure 3A:
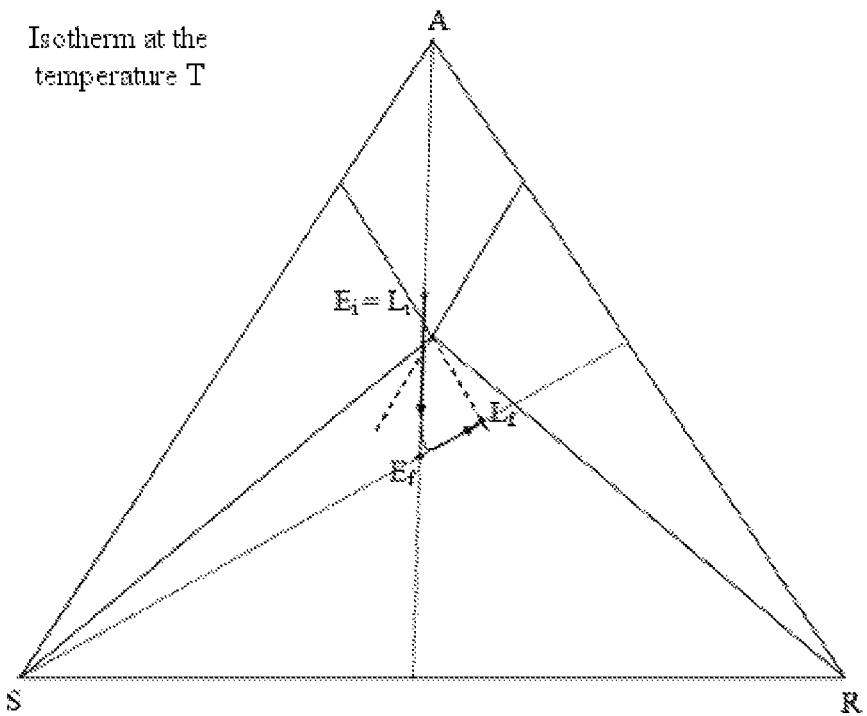
Figure 3B:
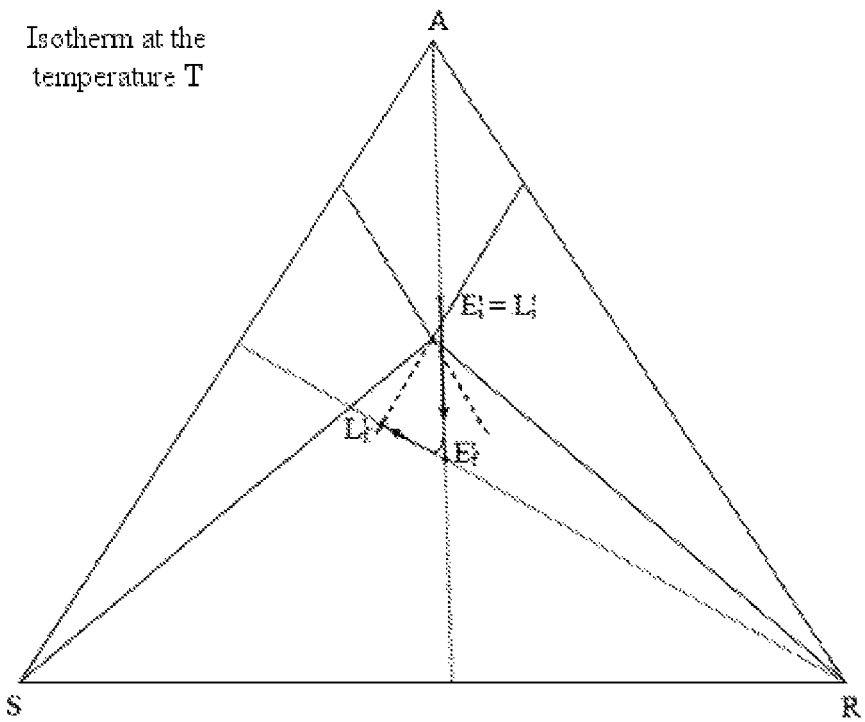
Figure 4:
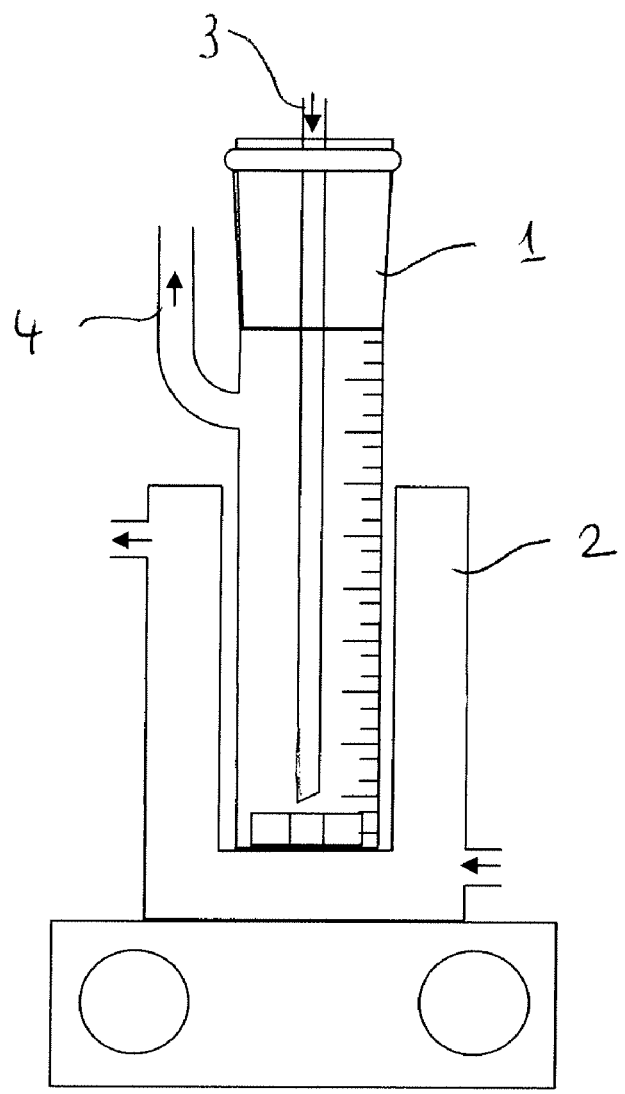
Figure 5:
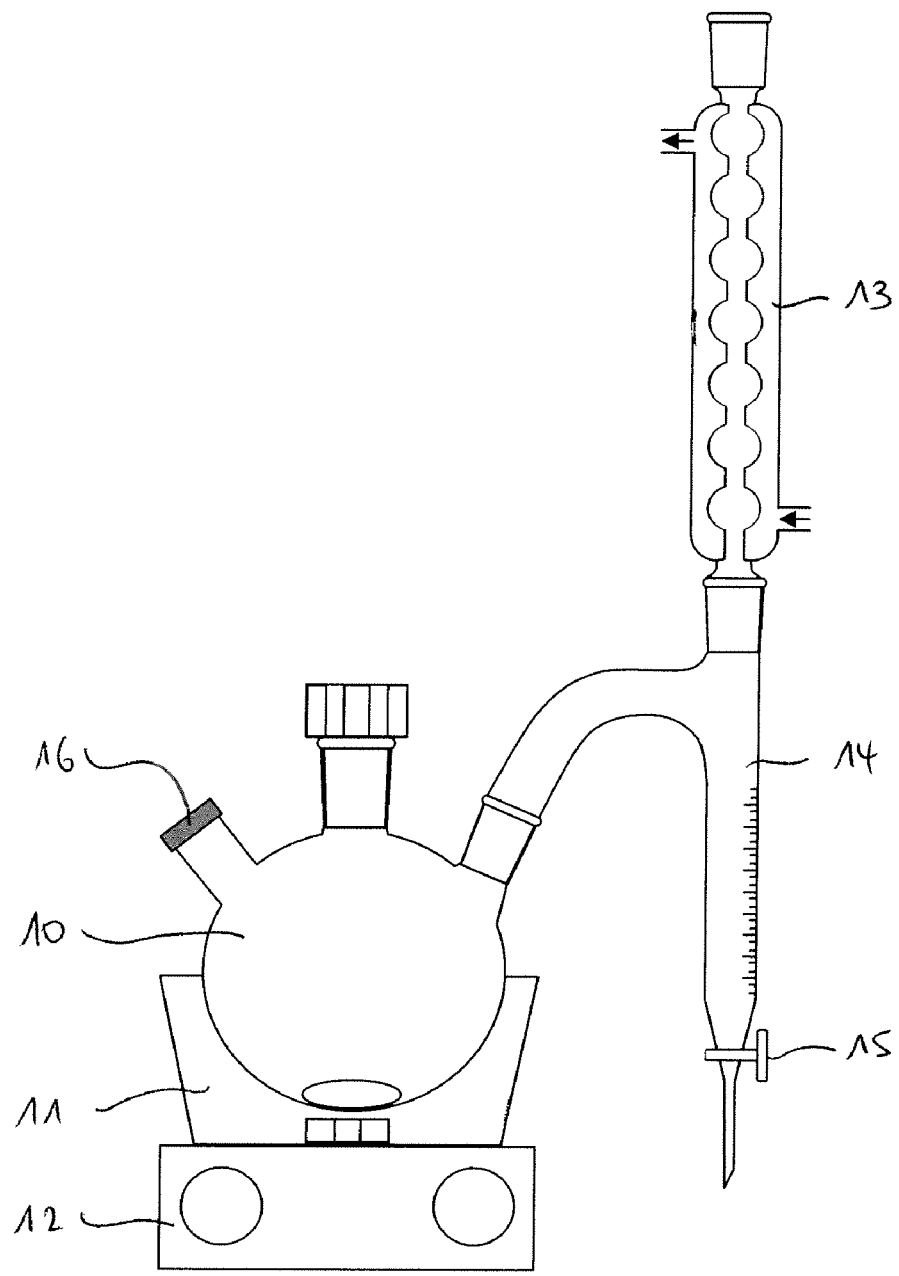
Figure 6:
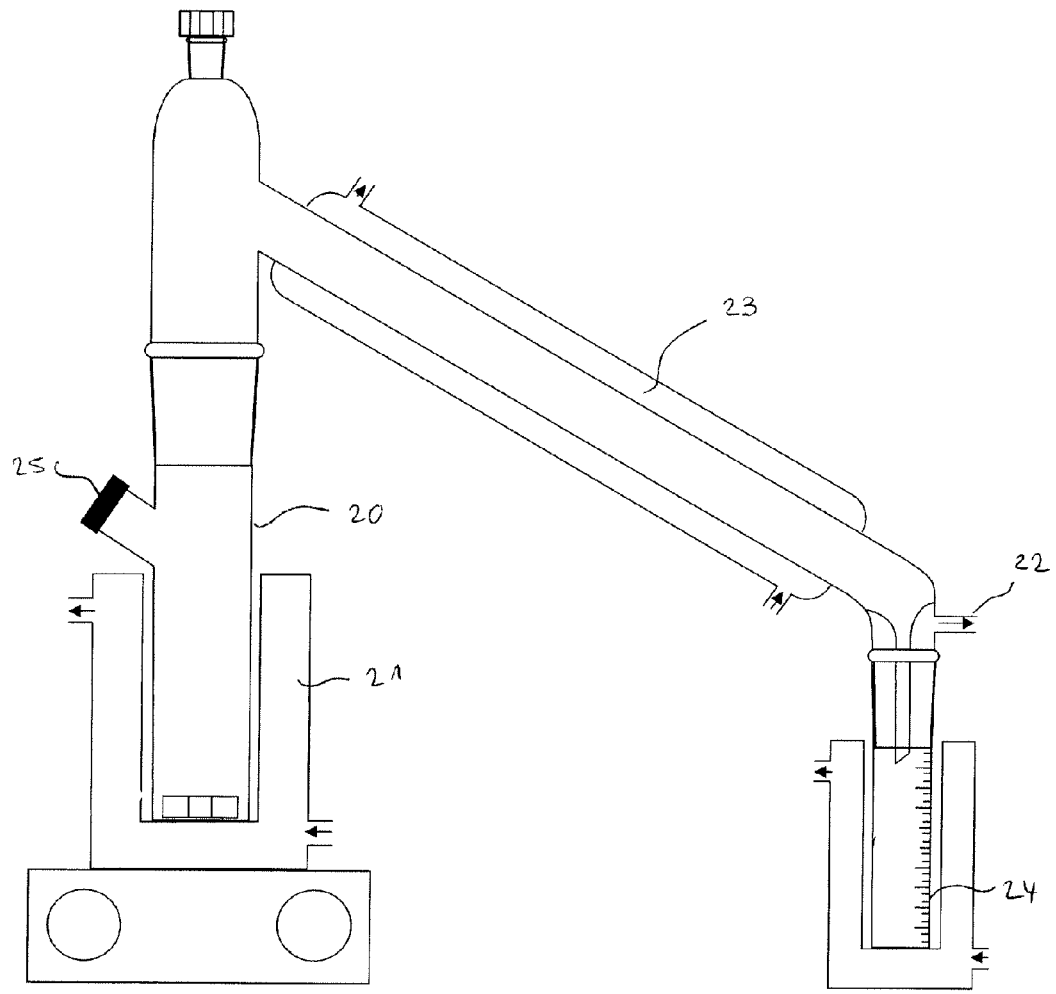

This process will now be described in more detail with reference to the appended figures, among which:

FIG. 1 represents the isothermal and isobaric section at the temperature T of a ternary diagram between a pair of enantiomers (R) and (S) and an achiral solvent (A), FIGS. 2A and 2B illustrate the change, on the isothermal section of FIG. 1, in the overall composition and in the liquid in a auto-seeded preferential evaporative crystallization process, FIGS. 3A and 3B illustrate the change, on the isothermal section of FIG. 1, in the overall composition and in the liquid in a seeded preferential evaporative crystallization process, FIG. 4 is a diagrammatic view of the equipment used for the evaporation under a stream of gas, FIG. 5 is a diagrammatic view of the equipment used for the evaporation at reflux, FIG. 6 is a diagrammatic view of the equipment used for the evaporation under vacuum.

In the implementation of the process according to the invention, the change in the composition of the system consisting of the enantiomers and the solvent can be monitored on a diagram such as that illustrated in FIG. 1. For purposes of simplification of this diagram, the solid phases are assumed to be nonsolvated and no miscibility in the solid state is supposed to be present. The section illustrated is located at a temperature where the solvent is in the liquid form, the melting point of the solvent being markedly lower than that of the enantiomers. At the working temperature and the working pressure, the pair of enantiomers crystallizes in the conglomerate form. This section of the ternary diagram can be divided into four regions:

1. Undersaturated solution: Region delimited by the diamond A-S(R)-S(R/S)-S(S). This region only comprises a single liquid phase.
2. Solution saturated with enantiomer S+crystals of S: Region delimited by the triangle S(S)-S-S(R/S). This region comprises a liquid phase (saturated with enantiomer S) and a solid phase (enantiomer S).
3. Solution saturated with enantiomer R+crystals of R: Region delimited by the triangle S(R)-R-S(R/S). This region comprises a liquid phase (saturated with enantiomer R) and a solid phase (enantiomer R).
4. Solution saturated with enantiomers R and S+crystals of R+crystals of S: Region delimited by the triangle R-S(R/S)-S. This region comprises three phases: two solid phases (crystals of R and of S) and one liquid phase (solution polysaturated with R and S).

In the first stage of the process according to the invention, a suspension or solution is prepared from a conglomerate of the enantiomers, from an excess of the first of the enantiomers and either from a single solvent or from a mixture of solvents, preferably an azeotropic mixture. Examples of solvents which can be used comprise, without limitation: ethanol, methanol, acetone, acetonitrile, water, heptane, ethyl acetate, dichloro-methane, methyl formate and their mixtures.

On conclusion of this stage, the suspension produced can be in the two-phase region of the enantiomer in excess at the working temperature T. Under these conditions, preferential dissolution of the enantiomer in deficit takes place, so that only the enantiomer in excess is present in the solid form and is used for the auto-seeding of the process. This situation is illustrated in FIG. 2A, where $E_i$ represents the overall composition of the suspension and $L_i$ represents the point representative of the liquid saturated with the enantiomer S. The latter is placed on the line representing the solubility of the enantiomer S.

In an alternative form, in the case where the process is seeded, the solution obtained on conclusion of the first stage is in the single-phase region, as illustrated by the point $E_i$ in FIG. 3A. The points $E_i$ and $L_i$ are in this case coincident since no crystal is present.

In the second stage, a partial evaporation of the solvent is carried out, preferably but not limitingly according to one of the three following techniques:

the application of a stream of gas, for example of a rare or neutral gas, such as argon or dinitrogen, or the extraction of the solvent at reflux, or the application of a negative pressure until the boiling pressure of the solvent is reached, or according to a combination of two or three of these techniques.

As illustrated in FIG. 4, the first of the above techniques can be employed in a tube (1) which is graduated, in order to measure the remaining volume of the suspension, and which is provided with a jacket (2) comprising a temperature-regulated (±0.1° C.) heat-exchange fluid. During the stages necessary for the evaporation of the solvent, the gas supplied by a bottle (not represented) is thermostatically controlled at the working temperature T, before being conveyed into the tube (1) via a hollow needle (3) immersed in the liquid. The stream of gas is then charged with solvent and is then discharged via the outlet (4).

In the second technique, illustrated in FIG. 5, the suspension is placed in a round-bottom flask (10), where the solvent is maintained at its boiling point, corresponding to the working temperature T, using an oil bath (11) and a heating plate (12). The vapor phase is condensed in a reflux condenser (13) and then falls into a Dean & Stark apparatus (14). During the equilibrating stages, the Dean & Stark apparatus is filled with solvent. The condensed solvent then falls back into the round-bottom flask (10). During stages requiring evaporation, the Dean & Stark apparatus (14) is emptied by virtue of a valve (15). The condensed solvent then falls into the Dean & Stark apparatus (14), so that it is isolated from the suspension present in the round-bottom flask (10). As the Dean & Stark apparatus (14) is graduated, it is easier to measure the volume of solvent evaporated. A septum (16) makes it possible to sample the suspension during the evaporation.

In the third technique, illustrated in FIG. 6, the suspension is placed in a container (20). The working temperature T is controlled inside the container by virtue of a jacket (21) comprising a temperature-regulated (±0.1° C.) heat-exchange fluid. During the stages requiring evaporation, the pressure is reduced using a pump connected at (22). The solvent evaporated from the tube (20) is condensed in a condenser (23) and then falls into a graduated container (24). The condenser (23) and the container (24) are thermostatically controlled using a heat-exchange fluid at the temperature $T_c$ ($T_c \ll T$), in order to limit the losses of solvent. The volume of solvent evaporated is measured by virtue of the graduations of the container (24). A septum (25) makes it possible to sample the suspension.

In addition to the abovementioned techniques, the evaporation of the solvent can be coupled with a temperature gradient, which can be induced by the loss in heat brought about by the evaporation of the solvent.

The evaporation process selected depends in particular on the vapor pressure of the solvent used. It is preferable in general to use the first and third techniques above for certain solvents, in particular volatile solvents, such as methanol, acetone or acetonitrile, for example.

The volume of solvent evaporated is sufficient for the overall synthetic mixture of the composition to be in the three-phase region at the temperature T, without, however, reaching the supersaturation limit of the second enantiomer, at which the spontaneous nucleation of the second enantiomer occurs. In practice, the amount of solvent evaporated is advantageously chosen so that twice the initial enantiomeric excess is crystallized at the time of the filtration.

If reference is made to FIG. 2A, in the case of an auto-seeded process, the point representative of the liquid, initially at the point $L_i$, tends to be displaced along the straight line $A-L_i$ in the direction of the point K during the evaporation of the solvent. At the same time, the point representative of the liquid gets closer to the metastable solubility (dotted line) of the enantiomer R, due to the crystallization of the latter. In practice, however, the path of the point representative of the liquid is different and depends on the rates of evaporation and of crystallization. The evaporation is interrupted when the point representative of the overall composition reaches the point $E_f$. The crystallization is interrupted when the point representative of the liquid has reached the point $L_f$.

In the case of a seeded process, as illustrated in FIG. 3A, when the solvent evaporates, the point representative of the overall composition of the system is displaced along the straight line $A-E_i$, the opposite way from the solvent point A, until a supersaturated solution is reached where no crystallization is observed. The supersaturated liquid is then seeded with a small amount of the pure enantiomer in excess or a suspension of this enantiomer in the solvent. The evaporation is subsequently continued until the overall synthetic mixture of the system reaches the point $E_f$. The crystallization of the enantiomer R then takes place stereoselectively and the point representing the overall composition of the liquid is displaced until the point $L_f$ is reached where the crystallization is complete.

In all the cases, the crystals of the first enantiomer are subsequently harvested. As the second enantiomer occurs in the metastable state in solution, the rate of filtration is adjusted in order to prevent it from crystallizing.

An amount by weight of racemic mixture, in the form of crystals, substantially identical to the weight of enantiomer collected above, and also solvent, are then added to the remaining mother liquor. The solvent is conventionally the same solvent or mixture of solvents as that used in stage 1, which can either be in the form of fresh solvent or of solvent resulting from the recovery of the solvent evaporated in stage 2. The amount of solvent added is adjusted so that the new overall synthetic mixture of the system is located in the two-phase region of the second enantiomer, at the working temperature T, in equilibrium with its saturated solution (auto-seeded process), or in the single-phase region (seeded process). More specifically, the new overall synthetic mixture $E'_i$, illustrated in FIGS. 2B and 3B, is positioned symmetrically to the point $E_i$, with respect to the median straight line passing through A on the isothermal section, at the temperature T, of the ternary diagram S-R-A.

The suspension or solution obtained is subsequently kept stirred at the temperature T until the thermodynamic equilibrium is reached. At this stage, in the case of the auto-seeded process, only the crystals of the second enantiomer in excess are present as solid phase in equilibrium with the saturated solution, the first enantiomer (undersaturated) being present only in the solution. In the case of the seeded process, only a liquid phase is observed.

The above stages of seeding (for the seeded process), of evaporation (as far as the point $E'_f$ illustrated in FIGS. 2B and 3B) and of harvesting are then repeated, this time promoting the crystallization of the second enantiomer, and then the overall composition of the system is readjusted in order to return to the point $E_i$, where the suspension or solution is kept stirred until the thermodynamic equilibrium is reached.

It is then understood that the replication of the preceding stages makes it possible to alternately obtain each of the two enantiomers. The distomer (undesired enantiomer) is preferentially racemized during an additional stage, in order to increase the yield of the process. The racemic mixture thus obtained can be reintroduced into the process described above, which makes it possible to achieve a yield of eutomer (desired enantiomer) of approximately 100%.

A better understanding of the present invention will be obtained in the light of the following examples, which are given purely by way of illustration and do not have the aim of limiting the scope of this invention defined by the appended claims.

EXAMPLES

Example 1

Alternating Preferential Crystallization of the Enantiomers of 5-methyl-5-phenylhydantoin a) Protocol The auto-seeded preferential crystallization process according to the invention was applied to the resolution of the (+) and (−) enantiomers of 5-methyl-5-phenylhydantoin.

To do this, 102.0 g of ethanol were mixed with 9.5 g of racemic mixture and 0.4 g of the pure (+) enantiomer (i.e., a total concentration $C_{tot}$ of active material of 9.2% by weight). The working temperature was 40° C. 18 ml of solvent were evaporated under vacuum with magnetic stirring over a period of 22 minutes. After evaporation, the suspension was filtered and 1.33 g ($w_{harvest}$) of solid were harvested, which solid has an optical purity O.P., determined by polarimetry, of 85.5% (that is to say, comprising 85.5% of the (+) enantiomer and 14.5% of racemic mixture), i.e. 1.14 g of pure (+) enantiomer. After filtration, the enantiomeric excess e.e.$_f$ of the mother liquor was −4.4% and the weight $w_{epf}$ of the (−) enantiomer in excess in the mother liquor was 0.33 g.

An additional amount of racemic mixture was then added to the mother liquor and the mixture was kept stirred at 40° C. for 30 minutes, before the beginning of the crystallization of the (−) enantiomer. An amount of solvent of 18 ml was subsequently again evaporated, over a time of 15.5 minutes. 1.07 g of crystals comprising 0.80 g of pure (−) enantiomer were recovered by filtration, so that the mother liquor comprised an enantiomeric excess of the (+) enantiomer. A fresh amount of racemic mixture was subsequently added to the mother liquor, which was kept stirred at 40° C. for 30 minutes. The preceding stages were then repeated, as illustrated in the table below:

| Crystallization No. | $C_{tot}$ (%) | Time (min) | O.P. (%) | $w_{harvest}$ (g) | $w_{pure\ enantiomer}$ (g) | e.e.$_f$ (%) | $w_{epf}$ (g) |
|---|---|---|---|---|---|---|---|
| 1 | 9.2 | 22 | 85.5 | 1.33 | 1.14 | −4.4 | 0.33 |
| 2 | 9.2 | 15.5 | 75.2 | 1.07 | 0.80 | 5.2 | 0.43 |
| 3 | 9.3 | 27 | 96.9 | 1.11 | 1.08 | −7.9 | 0.64 |
| 4 | 9.3 | 27 | 89.7 | 1.02 | 0.91 | 3.8 | 0.33 |
| 5 | 9.3 | 22 | 91.6 | 0.88 | 0.81 | −6.2 | 0.52 |
| 6 | 9.3 | 29 | 82.8 | 1.09 | 0.90 | 4.9 | 0.41 |
| 7 | 9.2 | 25 | 69.6 | 1.14 | 0.79 | −5.0 | 0.41 |
| 8 | 9.3 | 25 | 92.7 | 0.92 | 0.85 | 5.8 | 0.48 |
| 9 | 9.3 | 26 | 95.3 | 1.03 | 0.98 | −6.4 | 0.53 |
| 10 | 9.4 | 32 | 92.7 | 1.02 | 0.95 | 6.0 | 0.51 |
| 11 | 9.4 | 27 | 85.8 | 1.36 | 1.17 | −6.0 | 0.50 |
| 12 | 9.3 | 22 | 83.9 | 1.05 | 0.88 | 5.4 | 0.45 |
| 13 | 9.3 | 25 | 88.3 | 1.10 | 0.97 | −6.4 | 0.53 |
| 14 | 9.3 | 26 | 92.1 | 1.07 | 0.99 | 6.0 | 0.49 |
| mean | — | 25.0 | 87.3 | 1.08 | 0.94 | 5.7 | 0.47 |
| standard deviation | — | 3.9 | 7.6 | 0.13 | 0.12 | 1.0 | 0.08 | b) Results

The productive output of the ASPreCISE (for "Auto-Seeded PREferential Crystallization Induced by Solvent Evaporation") process according to the invention was compared with that of the preferential crystallization process described in U.S. Pat. No. 6,022,409 (referred to as "AS3PC").

The productive output P is defined by the following formula:

$$P = \frac{m}{w_{racemic\ mixture} \times (t_{evaporation} + t_{equilibrated})}$$

where:
w=weight of pure enantiomer ($w_{harvest} \times$O.P.) (g)
$w_{racemic\ mixture}$=weight of racemic mixture in the initial mixture (g)
$t_{equilibrated}$=duration of the evaporation of solvent (h)
$t_{evaporation}$=duration of the stirring at the evaporation temperature.

In this example, as the total duration of the evaporation and of the stirring is 55 minutes, the productive output according to the invention is equal to 0.1079 $g_{enantiomer}/g_{racemic\ mixture}/$h.

In the document U.S. Pat. No. 6,022,409 (columns 22 and 23), after reheating for 30 min at $T_B$ (starting temperature of the crystallization), the crystallization is carried out in 60 min. 0.569 g of crystals of pure enantiomer is harvested by filtration (O.P.=91%). The e.e.$_f$ of the mother liquor is 6.2%. The productive output is equal to 0.0804 $g_{enantiomer}/g_{racemic\ mixture}/$h.

The results (O.P. and e.e.$_f$) obtained by ASPreCISE and by AS3PC are comparable. The productive output is greater by the ASPreCISE method, mainly by virtue of a shorter crystallization time.

Example 2

Alternating Preferential Crystallization of the Enantiomers of Sodium 2-chloromandelate (i) Crystallization at the scale of 100 ml
a) Protocol
A similar process to that described in example 1 was followed, using the following initial parameters:

| weight methanol (g) | weight (±) (g) | weight (+) (g) |
|---|---|---|
| 45.0 | 10.0 | 1.0 | and the following crystallization conditions:
T=40° C.
Volume of solvent evaporated by crystallization=15 ml
Mean evaporation time=30 min
Duration of the stirring at 40° C. before the beginning of the crystallization=30 min
Crystallization Cycles:

| Crystallization No. | $C_{tot}$ (%) | Time (min) | O.P. (%) | $w_{harvest}$ (g) | $w_{pure\ enantiomer}$ (g) | e.e.$_f$ (%) | $w_{epf}$ (g) |
|---|---|---|---|---|---|---|---|
| 1 | 22.2 | 30 | 61.3 | 1.53 | 0.94 | 10.8 | 0.82 |
| 2 | 22.0 | 33 | 88.2 | 1.43 | 1.26 | −11.1 | 0.92 |
| 3 | 24.6 | 34 | 90.6 | 1.63 | 1.48 | 12.9 | 1.10 |
| 4 | 24.6 | 29 | 89.4 | 1.67 | 1.50 | −10.9 | 0.93 |
| 5 | 23.2 | 30 | 76.5 | 1.33 | 1.02 | −11.3 | 0.92 |
| 6 | 23.9 | 26 | 68.4 | 1.82 | 1.25 | 8.8 | 0.70 |
| 7 | 24.0 | 29 | 89.0 | 1.30 | 1.16 | −10.5 | 0.87 |
| 8 | 24.6 | 27 | 85.3 | 1.63 | 1.39 | 12.6 | 1.01 |

-continued

| Crystallization No. | $C_{tot}$ (%) | Time (min) | O.P. (%) | $w_{harvest}$ (g) | $w_{pure\ enantiomer}$ (g) | $e.e._f$ (%) | $w_{epf}$ (g) |
|---|---|---|---|---|---|---|---|
| 9 | 25.2 | 28 | 88.2 | 1.76 | 1.55 | −12.9 | 1.05 |
| 10 | 24.8 | 31 | 82.6 | 2.02 | 1.67 | 14.4 | 1.14 |
| 11 | 25.0 | 29 | 78.9 | 2.10 | 1.65 | −13.8 | 1.09 |
| mean | — | 29.6 | 81.7 | 1.66 | 1.35 | 11.8 | 0.96 |
| standard deviation | — | 2.4 | 9.6 | 0.26 | 0.25 | 1.6 | 0.13 | b) Result

The productive output was 0.1359 $g_{enantiomer}/g_{racemic\ mixture}/h$.

The difference in solubility of the racemic mixture between 40° C. and 20° C. is only 0.85% in absolute value. Sodium 2-chloromandelate thus comes within the products having a solubility not very dependent on the temperature. The resolution of the enantiomers thus cannot be carried out with correct yields according to the processes of the prior art.

(ii) Crystallization at the scale of a liter a) Protocol

Starting Conditions:

| weight methanol (g) | weight (±) (g) | weight (+) (g) |
|---|---|---|
| 450.0 | 100.0 | 5.0 |

Conditions Related to the Kinetics:

T=40° C.

Volume of solvent evaporated by crystallization=110 ml

Mean evaporation time=30 min

Duration of the stirring at 40° C. before the beginning of the crystallization=30 min Crystallization Cycles:

| Crystallization No. | $C_{tot}$ (%) | Time (min) | O.P. (%) | $w_{harvest}$ (g) | $w_{pure\ enantiomer}$ (g) | $e.e._f$ (%) | $w_{epf}$ (g) |
|---|---|---|---|---|---|---|---|
| 1 | 23.0 | 30 | 89.6 | 16.0 | 14.34 | 13.4 | 10.7 |
| 2 | 23.0 | 30 | 93.9 | 17.0 | 15.96 | −9.7 | 9.1 |
| 3 | 28.1 | 30 | 57.5 | 26.8 | 15.41 | 13.9 | 10.5 |
| 4 | 28.1 | 30 | 99.0 | 16.0 | 15.84 | −11.6 | 10.7 |
| 5 | 28.1 | 30 | 88.4 | 23.0 | 20.33 | 15.6 | 13.8 |
| 6 | 28.1 | 30 | 65.7 | 27.3 | 17.94 | −8.4 | 4.9 |
| mean | — | 30.0 | 82.4 | 21.0 | 16.6 | 12.1 | 9.9 |
| standard deviation | — | 0.0 | 16.7 | 5.4 | 2.2 | 2.7 | 2.9 | b) Result

The productive output was 0.166 $g_{enantiomer}/g_{racemic\ mixture}/h$.

Example 3

Alternating Preferential Crystallization of the Enantiomers of Sodium 2-chloromandelate a) Protocol A similar process to that described in example 2 was employed, except that the evaporation of the solvent was carried out at reflux and not under vacuum, with the following parameters.

Starting Conditions:

| weight methanol (g) | weight (±) (g) | weight (+) (g) |
|---|---|---|
| 51.0 | 15.0 | 0.5 |

Solubility of the racemic mixture in the methanol at reflux 23%

Conditions Related to the Kinetics:

$T_{oil\ bath}$=85° C.

Volume of solvent evaporated by crystallization=15 ml

Evaporation time=35 to 60 min

Duration of the stirring before the beginning of the crystallization=30 min

Crystallization Cycles:

| Crystallization No. | $C_{tot}$ (%) | Time (min) | O.P. (%) | $w_{harvest}$ (g) | $w_{pure\ enantiomer}$ (g) | $e.e._f$ (%) | $w_{epf}$ (g) |
|---|---|---|---|---|---|---|---|
| 1 | 26.2 | 37 | 80.2 | 0.90 | 0.72 | −4.0 | 0.55 |
| 2 | 27.3 | 53 | 88.9 | 0.77 | 0.68 | 2.6 | 0.40 |
| 3 | 27.3 | 38 | 77.6 | 1.11 | 0.86 | −5.7 | 0.78 |
| 4 | 29.3 | 63 | 82.1 | 1.44 | 1.18 | 6.3 | 0.91 |
| 5 | 29.1 | 43 | 88.5 | 0.95 | 0.84 | −5.1 | 0.73 |
| 6 | 28.4 | 33 | 82.3 | 1.26 | 1.04 | 6.1 | 0.80 |
| 7 | 27.4 | 53 | 86.8 | 1.08 | 0.94 | −4.4 | 0.69 |
| mean | — | 45.7 | 83.8 | 1.07 | 0.89 | 4.9 | 0.69 |
| standard deviation | — | 10.9 | 4.4 | 0.23 | 0.17 | 1.3 | 0.17 | b) Result

The productive output was 0.0470 $g_{enantiomer}/g_{racemic\ mixture}/h$.

Example 4

Alternating Preferential Crystallization of the Enantiomers of Sodium 2-chloromandelate a) Protocol A similar process to that described in example 3 was employed, except that the evaporation of the solvent was carried out under a stream of dinitrogen and not under vacuum, with the following parameters.

Starting Conditions:

| weight methanol (g) | weight (±) (g) | weight (+) (g) |
|---|---|---|
| 31.0 | 7.0 | 0.8 |

Conditions Relating to the Kinetics:

T=40° C.

Volume of solvent evaporated by crystallization=17 ml

Mean evaporation time=35 min

Duration of the stirring before the beginning of the crystallization=30 min

Crystallization Cycles:

| Crystallization No. | $C_{tot}$ (%) | Time (min) | O.P. (%) | $w_{harvest}$ (g) | $w_{pure\ enantiomer}$ (g) | $e.e._f$ (%) | $w_{epf}$ (g) |
|---|---|---|---|---|---|---|---|
| 1 | 27.5 | 32 | 89.3 | 1.16 | 1.04 | −8.9 | 0.65 |
| 2 | 29.1 | 35 | 84.5 | 1.04 | 0.88 | 9.8 | 0.75 |
| 3 | 28.9 | 34 | 86.2 | 1.19 | 1.02 | −10.3 | 0.76 |

-continued

| Crystallization No. | $C_{tot}$ (%) | Time (min) | O.P. (%) | $w_{harvest}$ (g) | $w_{pure\ enantiomer}$ (g) | e.e.$_f$ (%) | $w_{epf}$ (g) |
|---|---|---|---|---|---|---|---|
| 4 | 29.1 | 42 | 84.9 | 1.12 | 0.95 | 10.2 | 0.78 |
| 5 | 26.6 | 33 | 86.2 | 1.31 | 1.13 | −11.8 | 0.91 |
| 6 | 27.5 | 35 | 86.5 | 1.35 | 1.17 | 11.2 | 0.84 |
| 7 | 27.1 | 34 | 88.5 | 1.29 | 1.14 | −11.9 | 0.88 |
| 8 | 27.2 | 33 | 86.1 | 1.57 | 1.35 | 13.5 | 1.01 |
| 9 | 27.2 | 35 | 88.1 | 1.61 | 1.42 | −13.4 | 1.03 |
| 10 | 27.0 | 37 | 88.5 | 1.49 | 1.32 | 11.2 | 0.86 |
| mean | — | 34.9 | 86.9 | 1.31 | 1.14 | 11.2 | 0.85 |
| standard deviation | — | 2.9 | 1.6 | 0.20 | 0.18 | 1.5 | 0.12 | b) Result

The productive output was 0.1503 $g_{enantiomer}/g_{racemic\ mixture}/h$.

The invention claimed is:

1. Process for the resolution of two enantiomers by auto-seeded preferential evaporative crystallization, which comprises the stages consisting in:
   1) Preparing a suspension comprising a racemic mixture of enantiomers, an excess of the first of the enantiomers and at least one solvent, at a temperature T, so that the overall synthetic mixture $E_i$ representing the composition of the suspension, on the isothermal section at T of the ternary diagram between the pair of enantiomers and the solvent, is located in the two-phase region of the enantiomer in excess, in equilibrium with its saturated solution;
   2) Evaporating a portion of the solvent present in the suspension prepared in 1) until a overall synthetic mixture $E_f$ is reached located in the three-phase region of said ternary diagram;
   3) Harvesting the crystals of the first enantiomer by filtration;
   4) Adding, to the mother liquor resulting from the preceding filtration, the racemic mixture in the form of crystals, and also solvent, so that the overall composition of the system is represented by the point $E'_i$, symmetrical to the point $E_i$, with respect to the plane of the racemic mixture of the system on said isothermal section;
   5) Leaving the suspension stirring at the temperature T until the thermodynamic equilibrium is reached;
   6) Evaporating substantially the same amount of solvent as during stage 2), so that the overall synthetic mixture reaches a point $E'_f$ located in the three-phase region of said ternary diagram;
   7) Harvesting the crystals of the second enantiomer by filtration;
   8) Adding, to the mother liquor resulting from the preceding filtration, the racemic mixture in the form of crystals, and also solvent, so that the overall composition of the system is represented by the point $E_i$ on said isothermal section;
   9) Leaving the suspension stirring at the temperature T until the thermodynamic equilibrium is reached;
   10) Repeating stages 2) to 9) in order to successively obtain one and then the other of the enantiomers.

2. Process for the resolution of two enantiomers by seeded preferential evaporative crystallization, which comprises the stages consisting in:
   1) Preparing a homogeneous solution comprising a racemic mixture of the enantiomers, an excess of the first of the enantiomers and at least one solvent, at a temperature T, so that the point $E_i$ representing the composition of the solution, on the isothermal section at T of the ternary diagram between the pair of enantiomers and the solvent, is located in the single-phase region;
   2) Evaporating a portion of the solvent present in the solution prepared in 1), in order to obtain a supersaturated solution;
   3) Seeding the solution with the enantiomer in excess;
   4) Again evaporating a portion of the solvent, so that the overall synthetic mixture reaches a point $E_f$ located in the three-phase region of said ternary diagram;
   5) Harvesting the crystals of the first enantiomer by filtration;
   6) Adding, to the mother liquor resulting from the preceding filtration, the racemic mixture in the form of crystals, and also solvent, so that the overall composition of the system is represented by the point $E'_i$ symmetrical to the point $E_i$, with respect to the plane of the racemic mixture of the system on said isothermal section;
   7) Leaving the solution stirring at the temperature T until dissolution is complete;
   8) Evaporating substantially the same amount of solvent as during stage 2);
   9) Seeding the solution with the second enantiomer in excess;
   10) Evaporating substantially the same amount of solvent as during stage 4), so that the overall synthetic mixture reaches a point $E'_f$ located in the three-phase region of said ternary diagram;
   11) Harvesting the crystals of the second enantiomer by filtration;
   12) Adding, to the mother liquor resulting from the preceding filtration, the racemic mixture in the form of crystals, and also solvent, so that the overall composition in the system is represented by the point $E_i$ on said isothermal section;
   13) Leaving the solution stirring at the temperature T until the thermodynamic equilibrium is reached;
   14) Repeating stages 2) to 13) in order to successively obtain one and then the other of the enantiomers.

3. Process according to claim 1, which is applied to the resolution of the enantiomers of sodium 2-chloromandelate or of 5-methyl-5-phenylhydantoin.

4. Process according to claim 1, wherein the solvent is chosen from: ethanol, methanol, acetone, acetonitrile, water, heptane, ethyl acetate, dichloromethane, methyl formate and their mixtures.

5. Process according to claim 1, wherein the solvent is evaporated according to any one of the following techniques:
   the application of a stream of gas, or
   the extraction of the solvent at reflux, or
   the application of a negative pressure, down to the boiling pressure of the solvent,
or according to a combination of two or three of these techniques.

6. Process according to claim 1, wherein the amount of solvent evaporated is chosen in such a way that twice the initial enantiomeric excess is crystallized at the moment of the filtration.

7. Process according to claim 1, which comprises an additional stage of racemization of the distomer.

8. Process according to claim 2, which is applied to the resolution of the enantiomers of sodium 2-chloromandelate or of 5-methyl-5-phenylhydantoin.

9. Process according to claim 2, wherein the solvent is chosen from: ethanol, methanol, acetone, acetonitrile, water, heptane, ethyl acetate, dichloromethane, methyl formate and their mixtures.

10. Process according to claim 2, wherein the solvent is evaporated according to any one of the following techniques:
   the application of a stream of gas, or
   the extraction of the solvent at reflux, or
   the application of a negative pressure, down to the boiling pressure of the solvent,
or according to a combination of two or three of these techniques.

11. Process according to claim 2, wherein the amount of solvent evaporated is chosen in such a way that twice the initial enantiomeric excess is crystallized at the moment of the filtration.

12. Process according to claim 2, which comprises an additional stage of racemization of the distomer.

* * * * *